United States Patent [19]
Collins, Jr.

[11] Patent Number: 5,645,424
[45] Date of Patent: Jul. 8, 1997

[54] MANDIBULAR ADVANCEMENT APPLIANCE

[76] Inventor: John Albert Collins, Jr., 1116 Mishawaka Ave., South Bend, Ind. 46615

[21] Appl. No.: 531,360

[22] Filed: Sep. 20, 1995

Related U.S. Application Data

[63] Continuation-in-part of Ser. No. 258,047, Jun. 10, 1994.
[51] Int. Cl.$^6$ ............................................. A61C 7/00
[52] U.S. Cl. ............................... 433/21; 433/18; 433/19
[58] Field of Search ................................ 433/18, 19, 17, 433/20, 21, 22

[56] References Cited

U.S. PATENT DOCUMENTS

| | | | |
|---|---|---|---|
| 4,239,487 | 12/1980 | Murdock | 433/7 |
| 4,424,032 | 1/1984 | Howe | 433/19 |
| 4,433,956 | 2/1984 | Witzig | 433/7 |
| 4,472,139 | 9/1984 | Rosenberg | 433/19 |
| 4,551,095 | 11/1985 | Mason | 433/19 |
| 4,618,324 | 10/1986 | Nord | 433/19 |
| 4,619,609 | 10/1986 | Clark | 433/6 |
| 4,708,646 | 11/1987 | Jasper | 433/19 |
| 5,064,370 | 11/1991 | Jones | 433/21 |
| 5,066,226 | 11/1991 | Summer | 433/19 |
| 5,306,142 | 4/1994 | Richards | 433/17 |

OTHER PUBLICATIONS

Advertising Brochure for CorMar, Inc. Spring Coil Bushing from AOA, undated.
Advertising Brochure for the Jasper Jumper Appliances from AOA, undated.
Advertising for "Fixed Bionator" appliance from Ohlendorf Company, dated Jun. 1989.
Advertising Brochure for the Herbst appliances from AOA, undated.
Advertising for modified Herbst appliance from TP Orthodontics, Inc., 1992.
"Physiologic Principles of Functional Appliances," Thomas M. Graber, 1985.
Advertising Brochure for ORMCO Bite Jumping Appliance--Herbst Therapy, 1992.
Advertisement for "MALU–Mobee lock" system, Saga Dental.
Advertisement for Herbst IV Appliance, Journal of Clinical Orthodontics, May 1995.
Advertisement for Herbst Appliance Lab Services for Specialty Appliances, Journal of Clinical Orthodontics, May 1995.
Carlos Martins Coelho Filho, DDS, "Mandibular Protraction Appliances for Class II Treatment," Journal of Clinical Orthodontics, May 1995.

*Primary Examiner*—Cary E. O'Connor
*Attorney, Agent, or Firm*—Kenyon & Kenyon

[57] ABSTRACT

An orthodontic appliance which may be used to advance the mandible comprising a central straight segment, a pair of pivotable connectors disposed at opposite ends of the central straight segment, and a pair of arms each extending from one of the oppositely disposed pivotable connectors. The arms may be affixed, oppositely directed, to opposing upper and lower teeth on one side of a patient's dental arch.

18 Claims, 2 Drawing Sheets

MANDIBULAR ADVANCEMENT APPLIANCE

CROSS REFERENCE TO RELATED APPLICATION

The subject application is a continuation-in-part of U.S. Ser. No. 08/258,047 filed Jun. 10, 1994, pending.

FIELD OF INVENTION

The present invention is directed to an orthodontic appliance for use in interarch correction, and more particularly to a mandibular advancement appliance which may be used for fixed or removable applications.

BACKGROUND OF THE INVENTION

Various methods of orthodontic treatment have been used to effect advancement of the mandible. The methods can be broken down into two categories: those using removable appliances and those using fixed appliances.

Removable appliances are often popular with patients due to controllable and limited wear time while still achieving good results. However, such treatment also includes the risks associated with failure of patient compliance. A patient's inability or unwillingness to wear an appliance for the prescribed period of time may lengthen treatment time or compromise the results achieved. Further, orthodontists often disfavor the use of removable appliances because of a patient's failure to cooperate or because the continuous removal and replacement of an appliance necessitates constant adjustment. Fixed appliances, though often popular among orthodontists because of reduced treatment time and better results, are often disfavored by patients. This is particularly true of the prior art fixed mandibular advancement devices. They are generally anchored to the teeth in the upper first molar buccal area and lower first bicuspid or cuspid buccal area with bulky connecting arms designed for advancement of the mandible. Such bulky appliances are not aesthetically pleasing and in some cases cause considerable discomfort. This may lead to patient rejection or non-acceptance of the appliance.

One prior art mandibular advancement device is the Herbst appliance. Briefly, the Herbst appliance and its modified versions include a central positioning rod operatively disposed between the upper and lower dental arches and anchored at opposite ends to bands or other framework on the teeth. The appliance is designed to advance the mandible or effect other jaw movements. The central positioning rod is relatively bulky to provide structural integrity. The overall device is made more bulky due to the connecting arms designed to secure the central positioning rod at opposing ends to the bands on the teeth. The connecting arms secure the central rod in place and allow hinged movement for opening and closing of the jaw. Each connecting arm comprises a separate securing element, such as a screw, to attach the central positioning rod to bands on the teeth. The screw is inserted through an eyelet in the rod and affixed to the band. The screw, thus secures the rod in place and also allows pivoting of the rod when the jaw is opened and closed. This device is bulky, is not aesthetically pleasing and is not comfortable to wear.

Another device used for effecting jaw movements is known as the Jasper Jumper and is essentially described in U.S. Pat. No. 4,708,646. The appliance includes a central positioning spring which is operatively connected at its opposing ends to the opposing dental arches. The device is affixed to bands or brackets on a patient's teeth by separate attachment components such as hook and eyelet means. The spring creates a continuous force, and the attachment components additionally allow for the opening and closing of a patient's jaw. This device includes several separate pieces and is also bulky within a patient's mouth creating patient discomfort.

SUMMARY OF THE INVENTION

In view of the shortcomings and disadvantages associated with the prior mandibular advancement devices, it is an object of the present invention to provide an orthodontic appliance which can be used in either removable or fixed applications and which would be compatible with most appliance systems.

It is another object of the present invention to provide an orthodontic appliance which corrects a plurality of jaw misconfigurations with reduced treatment time.

It is a further object of the present invention to provide an orthodontic appliance which has a unique anchorage system to allow for improved range of motion of the mandible and which is comfortable to wear.

It is a further object of the present invention to provide a mandibular advancement appliance which is durable, but which does not include the bulk normally associated with such devices.

It is a further object of the present invention to provide for an orthodontic appliance which effects jaw movements and which simultaneously provides superior comfort and aesthetics.

It is a further object of the present invention to provide an interarch correction appliance that operates as a universal left/right part and can be used to either advance the mandible or distalize molars.

Briefly, the present invention provides for an orthodontic appliance which may be used for interarch correction comprising a central straight segment with a first end and a second end, a first pivotable connector contiguous to the first end of the central straight segment, and a first arm contiguous to the first pivotable connector and extending in a first direction, a second pivotable connector contiguous to the second end of the central straight segment, and a second arm contiguous to the second pivotable connector and extending in a second direction generally opposite the first direction.

Other objectives and advantages will become apparent upon reading the detailed description which follows.

DETAILED DESCRIPTION

Figure 1:
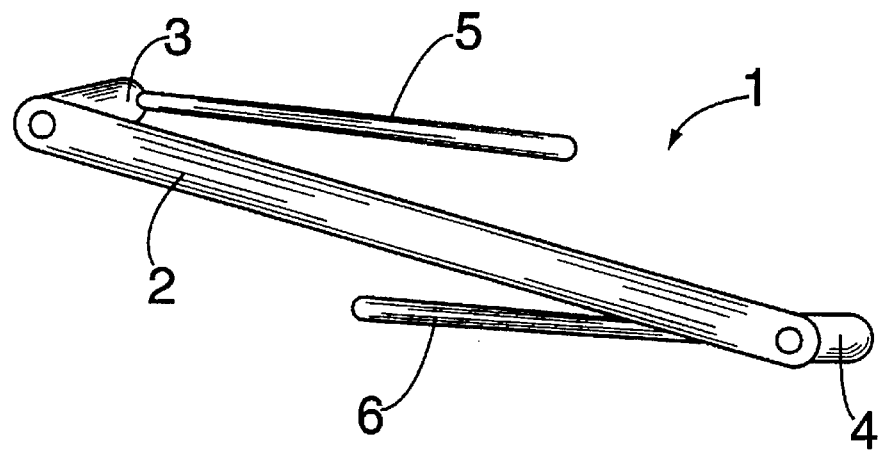
FIG. 1 is a perspective view of the orthodontic appliance of the present invention.
Figure 2:
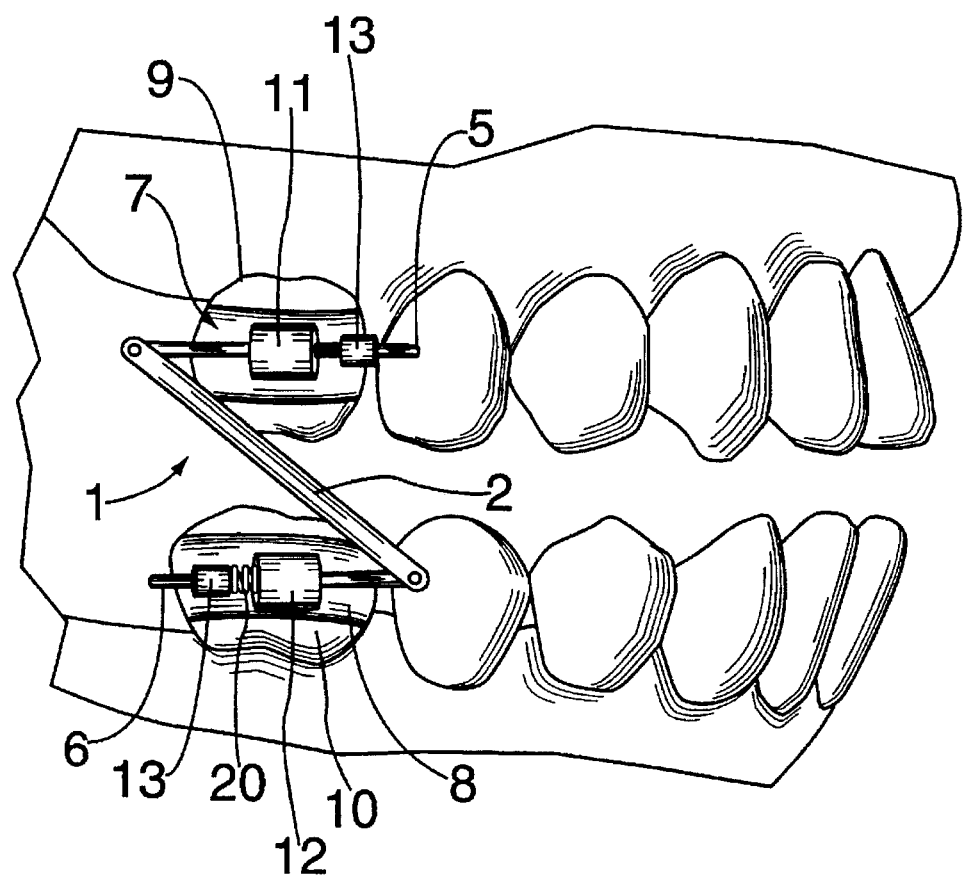
FIG. 2 is a plan view of the orthodontic appliance of the present invention in place inside the mouth of a patient as attached to the buccal surface of bands affixed to a patient's first molars.

Referring to the drawings, FIGS. 1 and 2 illustrate an orthodontic appliance constructed in accordance with the present invention. Generally, the appliance 1 may be of any suitable material, such as stainless steel or titanium. The appliance 1 is fabricated to include a central shaft 2, two pivotable connectors 3 and 4 and two articulation arms 5 and 6.

Figure 3:
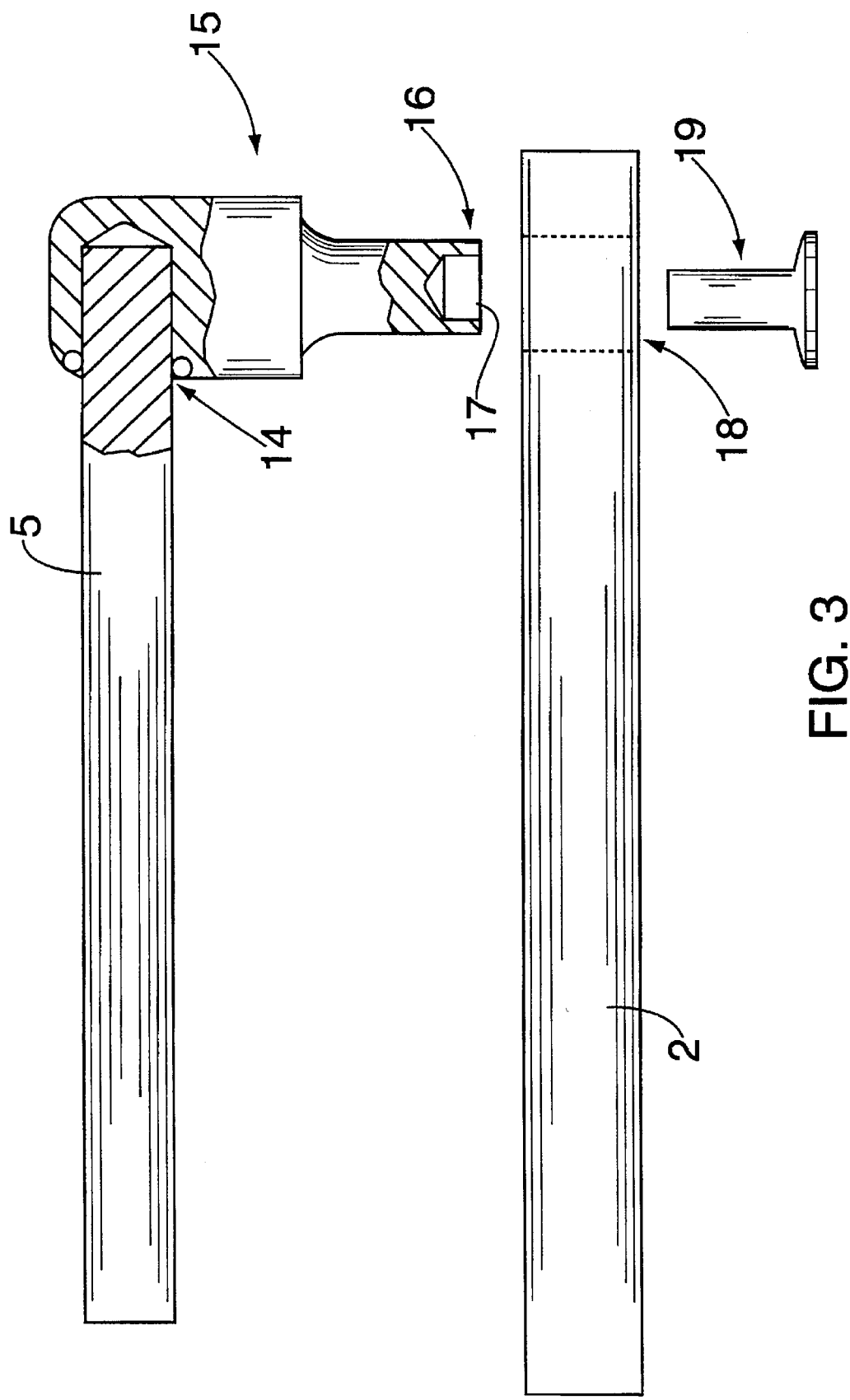
FIG. 3 depicts a pivotable connector which may be used in accordance with the present invention.

A set of pin swivel hinges are preferred as pivotable connectors in the present invention. As shown in FIG. 3, the pin swivel hinge comprises an articulation arm 5 received in a lateral hole 14 bored in the side of connector 15. The articulation arm 5 is secured in connector 15 by induction soldering. At the connector end 16, the connector is inserted through a hole 18 in the central shaft 2. The connector/articulation arm assembly is then secured to central shaft 2 by pin 19 which inserts through hole 18 into a longitudinal hole 17 bored in connector end 16. The pin 19 is secured in the connector end 16 by induction soldering. This pin swivel hinge assembly provides a free range of movement of the articulation arm 5 relative to central shaft 2 about the axis of the shaft of pin 19.

The appliance 1 may be affixed to a patient's upper and lower dental arches to effect advancement of the mandible or to effect distalization of molars. Preferably, the appliances is affixed to a patient's opposing upper and lower first molars.

FIG. 2 represents the orthodontic appliance of the present invention in place inside a patient's mouth. Metallic bands 7 and 8 are seated around upper first molar 9 and lower first molar 10. The bands may be affixed to the teeth by any conventional means such as with cement glue. The bands 7 and 8 have attachment means such as metallic tubes 11 and 12 affixed thereto. Where a tube is employed, the tube opening (not shown) may be round or rectangular in cross section, but is large enough for the passage of articulation arms 5 or 6 of the appliance of the present invention.

To effect advancement of the mandible, the orthodontic appliance may be secured in place by inserting opposing articulation arms 5 and 6 through tubes 11 and 12. The tube 11 affixed to the band on the upper first molar 9 receives the first arm 5 of the orthodontic appliance initially through the distal opening of the tube, such that when the appliance 1 is in place, the free tip of the first arm 5 points forward in the patient's mouth and the first pivotable connector 3 is directed distally. Alternately, the tube 12 affixed to the band on the lower first molar 10 receives the second arm 6 initially through the mesial opening of the tube such that when the appliance 1 is in place, the free tip of the second arm 6 points in the distal direction in the patient's mouth and the second pivotable connector 4 is directed forward in the patient's mouth. The arms 5 and 6 are secured in place by means of metallic crimpable or adjustable stops 13. Stainless steel adjustable Allen-head stops are preferred to allow for incremental advancement. Other means of securing arms 5 and 6 may be employed. The appliance may also optionally be used with a nickel titanium spring 20 as shown in FIG. 2. The spring may be disposed about an arm and abut the attachment means at one end of the spring and abut the stop at the other end of the spring.

In place on the buccal surface of opposing first molars, the pivotable connectors are positioned to allow clearance upon jaw closure, while at the same time securing the appliance close to the buccal surface of the teeth to prevent patient discomfort in the cheek area.

In a preferred embodiment, the central shaft 2 measures 28 to 45 mm in length and is 2.5 mm in diameter. Each articulation arm measures 16 mm and is 0.45 mm in diameter. The appliance is preferably made from 300 series stainless steel. However, other materials, such as 400 series stainless steel, 17-4 stainless steel, or titanium may also be used.

In use, the appliance of the present invention creates a continuous dynamic force which effects desired movement of the teeth. The device may be used for advancement of the mandible and/or for distalization of molars. A nickel titanium spring may be used in conjunction with the device, disposed about an articulation arm and creating a light continuous force, to assist and enhance molar distalization.

The pivotable connectors allow for normal jaw movement while speaking or eating and thus provide for patient comfort. The appliance may be used in conjunction with a wide variety of appliance systems in various phases of treatment and may be custom designed for fixed or removable applications. The appliance thus provides an improvement in patient comfort aesthetics and compliance, while shortening treatment time.

In the foregoing specification, the present invention has been described with respect to specific embodiments. These serve as examples to illustrate the invention rather than limit its scope. Modifications may be made without departing from the broader teachings and scope of the invention.

We claim:

1. A mandibular advancement assembly, comprising:
   two attachment means adapted to be affixed to each of a pair of opposing upper and lower teeth on one side of a patient's dental arch;
   an orthodontic appliance which includes a central straight segment, a pair of opposing pivotable connectors disposed at opposite ends of the central straight segment, and a pair of arms each extending from one of the oppositely disposed pivotable connectors;
   wherein the arms are each oppositely directed inward toward the central straight segment and secured in place by the attachment means; and
   wherein the attachment means, arms and pivotable connectors cooperate to allow full lateral movement of the upper and lower jaw when the arms of the orthodontic appliance are secured in place.

2. The mandibular advancement assembly of claim 1, wherein the attachment means are adapted to be affixed to the patient's upper and lower first molars on one side of the dental arch.

3. The mandibular advancement assembly of claim 1, wherein one or both of the attachment means includes a buccal tube which receives one of the appliance arms.

4. The mandibular advancement assembly of claim 1, further including an Allen head stop disposed at the distal end of one or both of the oppositely directed arms.

5. The mandibular advancement assembly of claim 1, further including a crimpable stop disposed at the distal end of one or both of the oppositely directed arms.

6. The mandibular advancement assembly of claim 1, wherein one or both of the pivotable connectors is a pin swivel hinge.

7. The mandibular advancement assembly of claim 1, wherein the orthodontic appliance is made from stainless steel.

8. The mandibular advancement assembly of claim 1, wherein the orthodontic appliance is made from titanium.

9. A molar distalizing assembly, comprising:
   two attachment means adapted to be affixed to each of a pair of opposing upper and lower teeth on one side of a patient's dental arch;
   an orthodontic appliance which includes a central straight segment, a pair of opposing pivotable connectors disposed at opposite ends of the central straight segment, and a pair of arms each extending from one of the oppositely disposed pivotable connectors;
   wherein the arms are each oppositely directed inward toward the central straight segment and secured in place by the attachment means; and wherein the attachment means, arms and pivotable cooperate to allow full lateral movement of the upper and lower jaw when the arms of the orthodontic appliance are secured in place.

10. The molar distalizing assembly of claim 9, wherein the attachment means are adapted to be affixed to the patient's upper and lower first molars on one side of the dental arch.

11. The molar distalizing assembly of claim 9, wherein one or both of the attachment means includes a buccal tube which receives one of the appliance arms.

12. The molar distalizing assembly of claim 9, further including a stop disposed at the distal end of one or both of the oppositely directed arms.

13. The molar distalizing assembly of claim 12, wherein the stop is a crimpable stop.

14. The molar distalizing assembly of claim 12, wherein the stop is a Allen head stop.

15. The molar distalizing assembly of claim 12, further including a nickel titanium spring disposed about one arm and abutting the attachment means at one end of the spring and abutting the stop at the other end of the spring.

16. The molar distalizing assembly of claim 9, wherein each of the pivotable connectors is a pin swivel hinge.

17. The molar distalizing assembly of claim 9, wherein the orthodontic appliance is made from stainless steel.

18. The molar distalizing assembly of claim 9, wherein the orthodontic appliance is made from titanium.

* * * * *